United States Patent
Ando et al.

(10) Patent No.: US 8,350,057 B2
(45) Date of Patent: Jan. 8, 2013

(54) METHOD FOR PRODUCING 3-METHYL-2-THIOPHENECARBOXYLIC ACID

(75) Inventors: Takayoshi Ando, Yokkaichi (JP); Norio Adachi, Kusatsu (JP); Akihiro Isogai, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 150 days.

(21) Appl. No.: 13/000,937

(22) PCT Filed: Jun. 25, 2009

(86) PCT No.: PCT/JP2009/061661
§ 371 (c)(1),
(2), (4) Date: Dec. 22, 2010

(87) PCT Pub. No.: WO2009/157525
PCT Pub. Date: Dec. 30, 2009

(65) Prior Publication Data
US 2011/0112311 A1    May 12, 2011

(30) Foreign Application Priority Data
Jun. 26, 2008    (JP) ................ 2008-167970

(51) Int. Cl.
C07D 333/40    (2006.01)
(52) U.S. Cl. ................................ 549/71
(58) Field of Classification Search ........ 549/71
See application file for complete search history.

(56) References Cited

FOREIGN PATENT DOCUMENTS

| EP | 0 109 381 A1 | 5/1984 |
|---|---|---|
| JP | 2001 247563 | 9/2001 |

OTHER PUBLICATIONS

Extended European Search Report issued Jan. 25, 2012, in Patent Application No. 09770235.1.
E. Campaigne, et al., "Synthesis of Unsymmetrical Arylthiophenes and Bithienyls via Oxidative Cyclization of 1,3-Butadiene-1-thiols", Journal of Heterocyclic Chemistry, vol. 25, XP 2667028, 1988, pp. 367-373.
Blanchette, J.A., et al., "The Willgerodt Reaction in the Heterocyclic Series. II. Some Compounds of the α- and β-Thienyl Series," Journal of the American Chemical Society, vol. 73, pp. 2779-2781, (Jun. 1951).
Lai, Y.-H., "Grignard Reagents from Chemically Activated Magnesium," Synthesis, vol. 8, pp. 585-604, (1981).
Campaigne, E., et al., "Chlorination of thiophenes with sulfuryl chloride," Journal of the American Chemical Society, vol. 70, pp. 415-416, (Jan. 1948).
Lamy, J., et al., "Thiophen Derivatives. Part XIII. Some Reactions of 3-Mehtylthiophen," Journal of the Chemical Society, pp. 4202-4205, (1958).
McGillivray, G., et al., "Chlorinations with t-buytl hypochlorite in the presence of alcohols. Part 2.[1] Effect of structure of the alcohol and order of the reactants, on the reactions of a substituted thiophene," South African Journal of Chemistry, vol. 42, No. 3, pp. 113-119, (1989).
Kamigata, N., et al., "Novel Halogenation of Thiophenes with Benzeneseleninyl Chloride and Aluminum Halide," Phosphorus, Sulfur and Silicon, vol. 53, pp. 29-35, (1990).
International Search Report issued Aug. 18, 2009 in PCT/JP09/061661 filed Jun. 25, 2009.

*Primary Examiner* — Taofiq A Solola
(74) *Attorney, Agent, or Firm* — Oblon, Spivik, McClelland, Maier & Neustadt, L.L.P.

(57) ABSTRACT

A method for producing 3-methyl-2-thiophenecarboxylic acid is provided.
A method for producing 3-methyl-2-thiophenecarboxylic acid, which comprises reacting a compound represented by the formula (I):

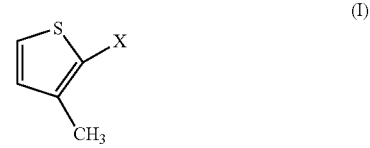

(I)

(wherein X is a chlorine atom or a bromine atom) with magnesium in the presence of an alkyl halide to give a Grignard reagent represented by the formula (II):

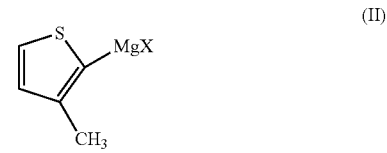

(II)

(wherein X is the same as defined above), reacting the Grignard reagent of the formula (II) with carbon dioxide, and acidifying the reaction product.

6 Claims, No Drawings

METHOD FOR PRODUCING 3-METHYL-2-THIOPHENECARBOXYLIC ACID

TECHNICAL FIELD

The present invention relates to a method for producing 3-methyl-2-thiophenecarboxylic acid useful as an intermediate for producing drugs and agrochemicals.

BACKGROUND ART

Patent Document 1 discloses a method for producing 3-methyl-2-thiophenecarboxylic acid which comprises reacting a 3,4-dihalobutan-2-one with a thioglycolic acid in the presence of a base. However, there are problems with industrial application of this method such as the use of malodorous thioglycolic acid.

Non-patent Document 1 discloses a method for producing 3-methyl-2-thiophenecarboxylic acid which comprises brominating 3-methylthiophene to 2-bromo-3-methylthiophene, preparing the Grignard reagent of 2-bromo-3-methylthiophene and reacting the Grignard reagent with carbon dioxide. However, this method cannot give 3-methyl-2-thiophenecarboxylic acid in sufficient yields.

PRIOR ART

Patent Document: JP-A-2001-247563
Non-patent Document: J. Am. Chem. Soc. 73, 2779-2781 (1951)

DISCLOSURE OF THE INVENTION

Object to be Accomplished by the Invention

Because 3-methyl-2-thiophenecarboxylic acid is useful as an intermediate for production of drugs and agrochemicals, it has been demanded to produce it easily, efficiently and more economically in an environmentally friendly manner. The production route from the compound of the after-mentioned formula (I) to 3-methyl-2-thiophenecarboxylic acid involving a reaction of the Grignard reagent of the formula (II) with carbon dioxide is of high industrial value, but under ordinary reaction conditions, even when relatively reactive 2-bromo-3-methylthiophene is used as the starting material, the conversion to the corresponding Grignard reagent is not satisfactory, and hence it is impossible to obtain 3-methyl-2-thiophenecarboxylic acid in high yields. On the other hand, when inexpensive 2-chloro-3-methylthiophene is used as the starting material, there is a problem that the corresponding Grignard reagent is hardly obtained because of its low reactivity.

The object of the present invention is to provide a method for producing 3-methyl-2-thiophenecarboxylic acid in a high yield easily, efficiently and more economically in an environmentally friendly manner.

Means to Accomplish the Object

As a result of their research for solutions to the above-mentioned problems, the present inventors found that the presence of an alkyl halide during preparation of a Grignard reagent improves the conversion to the Grignard reagent and raises the yield of 3-methyl-2-thiophenecarboxylic acid, and that it has the same effect even when a less reactive starting material such as 2-chloro-3-methylthiophene is used. The present invention was accomplished on the basis of the discovery.

Namely, the present invention provides a method for producing 3-methyl-2-thiophenecarboxylic acid, which comprises reacting a compound represented by the formula (I):

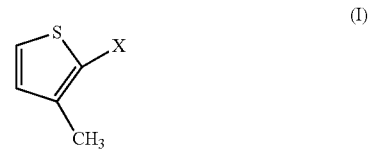

(wherein X is a chlorine atom or a bromine atom) with magnesium in the presence of an alkyl halide to give a Grignard reagent represented by the formula (II):

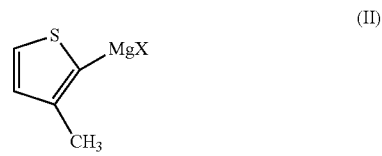

(wherein X is the same as defined above), reacting the Grignard reagent of the formula (II) with carbon dioxide, and acidifying the reaction product.

Advantageous Effects of the Invention

According to the present invention, it is possible to produce 3-methyl-2-thiophenecarboxylic acid useful as an intermediate for producing drugs and agrochemicals easily, efficiently and more economically in an environmentally friendly manner.

BEST MODE FOR CARRYING OUT THE INVENTION

Now, the method for producing 3-methyl-2-thiophenecarboxylic acid of the present invention will be described in detail with reference to the reaction flow charts.

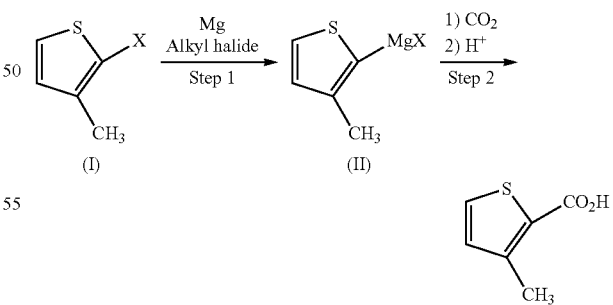

In the chart, X is the same as defined above.

The step 1 is production of a Grignard reagent of the formula (II) by a reaction of a compound of the formula (I) with magnesium in the presence of an alkyl halide, and because magnesium becomes more reactive upon activation by reacting with the alkyl halide, the desired Grignard reagent is produced efficiently. In the reaction, the compound of the formula (I), magnesium and the alkyl halide may be added at once, or in an arbitrary order, for example, by preliminarily reacting magnesium with an alkyl halide and adding an alkyl halide (which may be the same as or different from the previously added one) and the compound of the formula (I) simultaneously or separately, or by adding dropwise an alkyl halide to a mixture of the compound of the formula (I) and magnesium.

In the step 1, an alkyl halide comprising a $C_{1-6}$ alkyl substituted by a chlorine atom, a bromine atom or an iodine atom is used. Specifically speaking, methyl iodide, ethyl bromide, isopropyl bromide, ethylene dibromide, isopropyl chloride and the like may be mentioned. Among them, preferred are methyl iodide, ethyl bromide and isopropyl bromide, and ethyl bromide is more preferred. Alkyl halides may be used singly or in an appropriate combination of at least two.

The step 2 is production of 3-methyl-2-thiophenecarboxylic acid by reaction of the Grignard reagent of the formula (II) obtained in the step 1 with carbon dioxide followed by acidification of the reaction product.

In the present invention, the acidification means making the reaction system acidic by adding an acid or an aqueous acidic solution.

After the reaction, if necessary, 3-methyl-2-thiophenecarboxylic acid may be purified by an ordinary method, for example, by forming a salt with an alkali metal or an alkaline earth metal.

In the method of the present invention, 3-methyl-2-thiophenecarboxylic acid is produced through the above-mentioned steps 1 and 2, and usually, it is possible to carry out the reaction of the compound of the formula (I) with magnesium in the presence of an alkyl halide and the subsequent reaction with carbon dioxide and acidification successively.

It is usually possible to carry out the method of the present invention in the presence of a solvent throughout the steps 1 and 2. The solvent is not particularly limited as long as it does not adversely affect the reactions, and for example, ethers such as diethyl ether, tetrahydrofuran, tetrahydropyran, 1,4-dioxane, cyclopentyl methyl ether, diethoxyethane and methyl t-butyl ether; aromatic hydrocarbons such as benzene, toluene and xylene; saturated hydrocarbons such as normal paraffins, isoparaffins and naphthenes; and the like may be mentioned. As the solvent, one or more of them may be selected appropriately. Among these solvents, preferred are ethers, and tetrahydrofuran or tetrahydropyran is more preferred. If necessary, the solvent may be dehydrated by distillation or with a dehydrator before use. Although the amount of the solvent depends on the kinds of the raw material and the solvent and the reaction conditions and is not necessarily fixed, it is usually from 1 to 30 parts by weight, preferably from 2 to 10 parts by weight, based on 1 part by weight of the compound of the formula (I).

It is preferred to carry out the steps 1 and 2 in an atmosphere of an inert gas such as nitrogen, helium or argon because contact with water will reduces the yield.

In the present invention, although the amounts of the compound of the formula (I), magnesium, the alkyl halide and carbon dioxide depend on the kinds of the raw material and the solvent and the reaction conditions and are not necessarily fixed, they are usually used in the following amounts based on 1 mol of the compound of the formula (I): from 1.0 to 3.0 mol, preferably from 1.0 to 1.50 mol of magnesium, from 0.01 to 0.3 mol, preferably from 0.05 to 0.2 mol of the alkyl halide, and from 1.0 to 3.0 mol, preferably from 1.0 to 2.0 mol of carbon dioxide.

In the present invention, the reaction temperature and reaction time depend on the kinds and forms of the compound of the formula (I), magnesium, the alkyl halide, carbon dioxide and the solvent, the order of their addition, or their amounts and are not necessarily fixed.

However, in the step 1, the reaction temperature is usually from 0 to 150° C., preferably from 0 to 100° C., and the reaction time is from 0.1 to 24 hours, preferably from 1 to 10 hours.

In the step 2, the reaction temperature is usually from 0 to 150° C., preferably from 0 to 100° C., and the reaction time is from 0.1 to 24 hours, preferably from 0.5 to 10 hours.

In the present invention, various factors can be selected from the above-mentioned examples and conditions appropriately and combined. Namely, the kinds and forms of the compound of the formula (I), magnesium, the alkyl halide, carbon dioxide and the solvent, the order of their addition or their amounts; the reaction temperature; the reaction time and the like may be selected appropriately from usual or preferred examples and conditions and may be combined with one another.

The compound of the formula (I) can be produced by the following method.

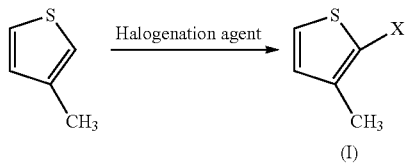

In the present invention, use of 2-chloro-3-methylthiophene as the compound of the formula (I) is economical and increases the industrial value of the method of the present invention.

2-Chloro-3-methylthiophene can be produced by various methods, for example, by reacting 3-methylthiophene with a chlorination agent.

The reaction of 3-methylthiophene with a chlorination agent for preparation of 2-chloro-3-methylthiophene may be carried out in the absence or presence of a solvent at a reaction temperature of from 0 to 150° C. for a reaction time of from 0.1 to 24 hours.

Specific examples of the chlorination agent to be used in the reaction for producing 2-chloro-3-methylthiophene include N-chlorosuccinimide (NCS), sulfuryl chloride and chlorine. Among them, sulfuryl chloride or chlorine is industrially preferred.

In the reaction for preparation of 2-chloro-3-methylthiophene, although the amount of the chlorination agent depends on the kinds of the raw material and the solvent and the reaction conditions and are not necessarily fixed, it is usually from 1.0 to 5.0 equivalents, preferably from 1.0 to 1.5 equivalents, based on 1 equivalent of 3-methylthiophene.

When the reaction for production of 2-chloro-3-methylthiophene is carried out in the presence of a solvent, the solvent is not particularly limited as long as it does not adversely affect the reaction, and for example, alcohols such as methanol and ethanol; acids such as acetic acid; nitriles such as acetonitrile; amides such as N,N-dimethylformamide and N,N-dimethylacetamide; halogenated hydrocarbons such as methylene chloride, chloroform, 1,2-dichloroethane and 1,1,2-trichloroethane; aromatic hydrocarbons such as benzene, toluene, xylene, nitrobenzene and chlorobenzene; saturated hydrocarbons such as normal paraffins, isoparaffins and naphthenes; esters such as methyl acetate, ethyl acetate and propyl acetate; ethers such as diethyl ether, 1,4-dioxane, tetrahydrofuran and 1,2-dimethoxyethane; nitrogen-containing aromatic compounds such as pyridine and quinoline; and the like may be mentioned. As the solvent, one or more of them may be selected appropriately. If necessary, the reaction may be carried out in an atmosphere of an inert gas such as nitrogen, helium or argon.

When the reaction for production of 2-chloro-3-methylthiophene is carried out in the presence of a solvent, though the amount of the solvent depends on the kinds of the raw material and the solvent and the reaction conditions and are not necessarily fixed, it is usually from 1 to 30 parts by weight, preferably from 1 to 10 parts by weight, based on 1 part by weight of 3-methylthiophene.

The following are preferred embodiments of the present invention. However, the present invention is not limited thereto.

(1) A method for producing 3-methyl-2-thiophenecarboxylic acid, which comprises reacting a compound represented by the formula (I) with magnesium in the presence of an alkyl halide to give a Grignard reagent represented by the formula (II), reacting the Grignard reagent of the formula (II) with carbon dioxide, and acidifying the reaction product.

(2) The method according to (1), wherein the compound of the formula (I) is 2-chloro-3-methylthiophene.

(3) The method according to (2), wherein 2-chloro-3-methylthiophene is obtained by reacting 3-methylthiophene with a chlorination agent.

(4) The method according to (3), wherein the chlorination agent is sulfuryl chloride or chlorine.

(5) The method according to any one of (1) to (4), wherein the alkyl halide is methyl iodide, ethyl bromide or isopropyl bromide.

Now, Examples of the present invention will be described, but it should be understood that the present invention is by no means thereby restricted.

EXAMPLES

Example 1

A four-neck flask equipped with a stirrer, a thermometer, a condenser tube and a dropping funnel was loaded with 11.8 g of magnesium and 250 mL of tetrahydrofuran in a nitrogen atmosphere, and 2.05 g of ethyl bromide was added and allowed to react under heating with reflux for 15 minutes. Then, while the reaction solution was refluxed, a liquid mixture of 50 g of 2-chloro-3-methylthiophene and 4.1 g of ethyl bromide was added dropwise and allowed to react under heating with reflux for 30 minutes. Then, 4.11 g of ethyl bromide was added and allowed to react under heating with reflux for another 1 hour.

Carbon dioxide was introduced into the resulting reaction solution at 25 to 35° C. and allowed to react at room temperature for 2 hours. After addition of water, the reaction solution was adjusted to pH 2 or below with concentrated hydrochloric acid. The aqueous layer was removed, and water was added to the organic layer. The solvent was evaporated to obtain a slurry of 3-methyl-2-thiophenecarboxylic acid. The slurry was filtered, and the residue was dried to obtain 50.5 g of 3-methyl-2-thiophenecarboxylic acid.

Example 2

A four-neck flask equipped with a stirrer, a thermometer, a condenser tube and a dropping funnel was loaded with 1.65 g of magnesium and 50 mL of tetrahydrofuran in a nitrogen atmosphere, and 0.69 g of isopropyl bromide was added and allowed to react under heating with reflux for 30 minutes. Then, while the reaction solution was refluxed, 10 g of 2-bromo-3-methylthiophene was added dropwise and allowed to react under heating with reflux for 30 minutes.

Carbon dioxide was introduced into the resulting reaction solution at 25 to 35° C. and allowed to react at room temperature for 2 hours. After addition of water, the reaction solution was adjusted to pH 2 or below with concentrated hydrochloric acid and extracted with ethyl acetate. After removal of the aqueous layer, the organic layer was dried over magnesium sulfate, and the solvent was evaporated to obtain 7.95 g of 3-methyl-2-thiophenecarboxylic acid.

Reference Example

Synthesis of 2-chloro-3-methylthiophene

A four-neck flask equipped with a stirrer, a thermometer, a condenser tube and a dropping funnel was loaded with 20 g of 3-methylthiophene, and 28.6 g of sulfuryl chloride was added dropwise at 15° C. or below and allowed to react at 15° C. or below for 1 hour.

The resulting reaction solution was diluted with ethyl acetate and washed with water and then with aqueous sodium hydroxide (10 wt % aqueous solution) to obtain a solution of 2-chloro-3-methylthiophene in ethyl acetate. The solution was distilled under reduced pressure to obtain 24.7 g of 2-chloro-3-methylthiophene with a boiling point of 84-86° C./120-133 hPa.

INDUSTRIAL APPLICABILITY

The method of the present invention can produce 3-methyl-2-thiophenecarboxylic acid useful as an intermediate for producing drugs and agrochemicals easily, efficiently and more economically in an environmentally friendly manner and therefore, is industrially useful.

The entire disclosure of Japanese Patent Application No. 2008-167970 filed on Jun. 26, 2008 including specification, claims and abstract is incorporated herein by reference in its entirety.

The invention claimed is:
1. A method for producing 3-methyl-2-thiophenecarboxylic acid, which comprises reacting a compound represented by the formula (I):

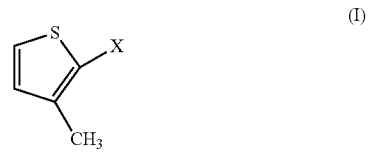

(wherein X is a chlorine atom or a bromine atom) with magnesium in the presence of an alkyl halide to give a Grignard reagent represented by the formula (II):

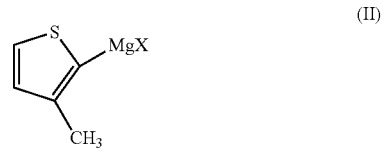

(wherein X is the same as defined above), reacting the Grignard reagent of the formula (II) with carbon dioxide, and acidifying the reaction product.

2. The method according to claim 1, wherein the compound of the formula (I) is a compound of the formula (I) wherein X is a chlorine atom.

3. The method according to claim 1 or 2, wherein the alkyl halide is methyl iodide, ethyl bromide or isopropyl bromide.

4. The method according to any one of claim 1, wherein the compound of the formula (I) is obtained by reacting 3-methylthiophene with a halogenation agent.

5. The method according to claim 4, wherein the halogenation agent is a chlorination agent.

6. The method according to claim 5, wherein the chlorination agent is sulfuryl chloride or chlorine.

\* \* \* \* \*

UNITED STATES PATENT AND TRADEMARK OFFICE
CERTIFICATE OF CORRECTION

PATENT NO.         : 8,350,057 B2
APPLICATION NO.    : 13/000937
DATED              : January 8, 2013
INVENTOR(S)        : Takayoshi Ando et al.

It is certified that error appears in the above-identified patent and that said Letters Patent is hereby corrected as shown below:

On the title page, Item (75), the 3$^{rd}$ Inventor's Name is incorrect. Item (75) should read:

--(75) Inventors: Takayoshi Ando, Yokkaichi (JP); Norio Adachi, Kusatsu (JP); Akihiko Isogai, Kusatsu (JP)--

Signed and Sealed this
Second Day of April, 2013

Teresa Stanek Rea
*Acting Director of the United States Patent and Trademark Office*